US012759961B2

(12) United States Patent
Weber et al.

(10) Patent No.: US 12,759,961 B2
(45) Date of Patent: Oct. 13, 2026

(54) REMOVAL OF ALDEHYDES IN ACETIC ACID PRODUCTION

(71) Applicant: LyondellBasell Acetyls, LLC, Houston, TX (US)

(72) Inventors: Shane J. Weber, League City, TX (US); Noel C. Hallinan, Loveland, OH (US); Ryan J. Mathews, Tomball, TX (US)

(73) Assignee: LyondellBasell Acetyls, LLC, Houston, TX (US)

( * ) Notice: Subject to any disclaimer, the term of this patent is extended or adjusted under 35 U.S.C. 154(b) by 834 days.

(21) Appl. No.: 18/111,088

(22) Filed: Feb. 17, 2023

(65) Prior Publication Data

US 2023/0265036 A1 Aug. 24, 2023

Related U.S. Application Data

(60) Provisional application No. 63/311,767, filed on Feb. 18, 2022.

(51) Int. Cl.
*C07C 51/12* (2006.01)
*B01D 3/06* (2006.01)
(Continued)

(52) U.S. Cl.
CPC ................ *C07C 51/12* (2013.01); *B01D 3/06* (2013.01); *B01D 3/143* (2013.01); *B01D 5/006* (2013.01);
(Continued)

(58) Field of Classification Search
CPC ......... C07C 51/12; C07C 51/44; C07C 51/47; B01D 3/06; B01D 3/143; B01D 5/006;
(Continued)

(56) References Cited

U.S. PATENT DOCUMENTS 5,416,237 A 5/1995 Aubigne et al.
5,620,567 A 4/1997 Seidel et al.
(Continued)

FOREIGN PATENT DOCUMENTS

CN 107986953 B 7/2021

OTHER PUBLICATIONS

The International Search Report and Written Opinion for PCT/US2023/013296 mailed Jun. 19, 2023.

*Primary Examiner* — Youngsul Jeong

(57) ABSTRACT

A system and method for removing acetaldehyde from an acetic acid system are disclosed. The method includes, providing a light-ends stream, comprising carbon monoxide, carbon dioxide, acetaldehyde, methyl iodide, methyl acetate, water, acetic acid, or mixtures thereof; condensing the light-ends stream to form one or more liquid phase compositions and a vapor phase composition, comprising a majority of the carbon monoxide and carbon dioxide and a minor portion of the acetaldehyde, methyl iodide, water, and acetic acid; contacting the vapor phase composition with a solvent to produce a liquid stream, comprising methyl iodide, acetaldehyde, and a portion of the solvent; and contacting the liquid stream, and optionally a polyol compound, with an acid catalyst to convert a portion of the acetaldehyde to an aldehyde derivative having a higher boiling point than acetaldehyde.

12 Claims, 3 Drawing Sheets

(51) Int. Cl.

| | |
|---|---|
| ***B01D 3/14*** | (2006.01) |
| ***B01D 5/00*** | (2006.01) |
| ***B01D 53/14*** | (2006.01) |
| ***B01J 31/08*** | (2006.01) |
| ***C07C 51/44*** | (2006.01) |
| ***C07C 51/47*** | (2006.01) |

(52) U.S. Cl.
CPC ..... *B01D 53/1431* (2013.01); *B01D 53/1487* (2013.01); *B01J 31/08* (2013.01); *C07C 51/44* (2013.01); *C07C 51/47* (2013.01); *B01J 2231/349* (2013.01); *B01J 2231/766* (2013.01); *B01J 2531/002* (2013.01)

(58) Field of Classification Search
CPC .. B01D 53/1431; B01D 53/1487; B01J 31/08; B01J 2231/349; B01J 2231/766; B01J 2531/002
See application file for complete search history.

(56) References Cited

U.S. PATENT DOCUMENTS 5,783,731 A * 7/1998 Fisher .................. C07C 51/487 562/519
5,817,869 A 10/1998 Hinnenkamp et al.
5,932,764 A 8/1999 Morris et al.
6,552,221 B1 4/2003 Hallinan et al.
7,345,197 B1 * 3/2008 Hallinan ................ C07C 51/48 562/607
7,390,919 B1 6/2008 Salisbury et al.
7,524,988 B2 * 4/2009 Harris .................. C07C 51/487 562/608
7,884,237 B2 2/2011 Shaver
8,076,506 B2 12/2011 Kimmich et al.
8,076,512 B2 12/2011 Fitzpatrick et al.
8,563,772 B2 10/2013 Shaver
8,969,613 B2 3/2015 Hallinan et al.
9,446,363 B2 9/2016 Zinoble et al.
9,662,646 B2 5/2017 You et al.
9,790,159 B2 10/2017 Hallinan et al.
10,010,841 B2 7/2018 Zinobile et al.
10,428,006 B2 10/2019 Miura et al.
2003/0199711 A1 * 10/2003 Broussard ............ C07C 51/487 562/519
2008/0051601 A1 * 2/2008 Sawyer ................ C07C 51/487 562/550
2011/0054213 A1 * 3/2011 Fitzpatrick ............. C07C 51/44 562/519
2020/0007971 A1 1/2020 Park et al.
2020/0079719 A1 * 3/2020 Shimizu ................. C07C 51/48

* cited by examiner

REMOVAL OF ALDEHYDES IN ACETIC ACID PRODUCTION

PRIOR RELATED APPLICATIONS

This application claims the benefit of priority to U.S. Provisional Application No. 63/311,767, filed on Feb. 18, 2022, the contents of which are incorporated herein by reference in their entirety.

FIELD OF THE INVENTION

This disclosure relates to the production of acetic acid. More particularly, the disclosure relates to removal of acetaldehyde in acetic acid production.

BACKGROUND OF THE INVENTION

In the current acetic acid production process, a reaction mixture is withdrawn from a reactor and is separated in a flash tank into a liquid fraction and a vapor fraction comprising acetic acid generated during the carbonylation reaction. The liquid fraction may be recycled to the carbonylation reactor, and the vapor fraction is passed to a separations unit, which by way of example may be a light-ends distillation column. The light-ends distillation column separates a crude acetic acid product from other components. The crude acetic acid product is passed to a drying column to remove water and then is subjected to further separations to recover acetic acid.

One challenge facing the industry is the presence of aldehyde(s) in acetic acid production, which can be present in the feed and also form as an undesired byproduct of carbonylation reactions. Processes for removing aldehydes exist; however, there continues to be a need to improve upon, and provide alternatives to, current aldehyde removal processes.

SUMMARY OF THE INVENTION

An aspect of the disclosure relates to a method for removing acetaldehyde from an acetic acid system, including: providing from the acetic acid system a light-ends stream, comprising carbon monoxide, carbon dioxide, acetaldehyde, methyl iodide, methyl acetate, water, acetic acid, or mixtures thereof; condensing the light-ends stream to form one or more liquid phase compositions and a vapor phase composition, wherein the one or more liquid phase compositions comprise a majority of the water and acetic acid, and the vapor phase composition comprises a majority of the carbon monoxide and carbon dioxide and a minor portion of the acetaldehyde, methyl iodide, water, and acetic acid; contacting the vapor phase composition with a solvent in an absorber to produce an absorber overhead vapor stream and an absorber bottoms liquid stream, wherein the absorber overhead vapor stream comprises carbon monoxide, carbon dioxide, and a first portion of the solvent, and the absorber bottoms liquid stream comprises methyl iodide, acetaldehyde, and a second portion of the solvent; and contacting a reactive feed stream, comprising the absorber bottoms liquid stream, and optionally a polyol compound, with an acid catalyst to form a reacted stream comprising an aldehyde derivative, wherein the aldehyde derivative is formed by conversion of at least a portion of the acetaldehyde and has a higher boiling point than acetaldehyde.

Another aspect of the disclosure relates to a method of operating an acetic acid production system, including: providing from the acetic acid system a light-ends stream, comprising carbon monoxide, carbon dioxide, acetaldehyde, methyl iodide, methyl acetate, water, acetic acid, or mixtures thereof; condensing the light-ends stream to form one or more liquid phase compositions and a vapor phase composition, wherein the one or more liquid phase compositions comprise a majority of the water and acetic acid, and the vapor phase composition comprises a majority of the carbon monoxide and carbon dioxide and a minor portion of the acetaldehyde, methyl iodide, water, and acetic acid; contacting the vapor phase composition with a solvent in an absorber to produce an absorber overhead vapor stream and an absorber bottoms liquid stream, wherein the absorber overhead vapor stream comprises carbon monoxide, carbon dioxide, and a first portion of the solvent, and the absorber bottoms liquid stream comprises methyl iodide, acetaldehyde, and a second portion of the solvent; and contacting a reactive feed stream, comprising the absorber bottoms liquid stream, and optionally a polyol compound, with an acid catalyst to form a reacted stream comprising an aldehyde derivative, wherein the aldehyde derivative is formed by conversion of at least a portion of the acetaldehyde and has a higher boiling point than acetaldehyde.

Yet another aspect relates to a method of producing acetic acid, including: reacting methanol and carbon monoxide in the presence of a carbonylation catalyst to form acetic acid in an acetic acid production reactor; flashing a reaction mixture discharged from the acetic acid production reactor into a vapor stream and a liquid stream, the vapor stream comprising acetic acid, methyl iodide, and acetaldehyde; and separating the vapor stream by distillation in a first distillation column into: (1) a product side stream 136 comprising acetic acid and water; (2) a first bottoms stream 131; and (3) a first overhead stream 132 comprising acetaldehyde, water, carbon monoxide, carbon dioxide, methyl iodide, methyl acetate, acetic acid, or mixtures thereof. The first overhead stream is condensed to form: (i) one or more liquid phase compositions; and (ii) a vapor phase composition, comprising a majority of the carbon monoxide and carbon dioxide and a minor portion of the acetaldehyde, methyl iodide, water, and acetic acid. The vapor phase composition is contacted with a solvent to produce a treated liquid stream, comprising methyl iodide, acetaldehyde, and a portion of the solvent. A reactive feed stream, comprising the treated liquid stream, and optionally a polyol compound, is contacted with an acid catalyst to form a reacted stream comprising an aldehyde derivative, wherein the aldehyde derivative is formed by conversion of at least a portion of the acetaldehyde and has a higher boiling point than acetaldehyde.

Yet another aspect of the disclosure relates to an acetic acid production system, having: an acetic acid production reactor to react methanol and carbon monoxide in the presence of a carbonylation catalyst to form acetic acid; a flash vessel that receives a reaction mixture comprising the acetic acid from the reactor; a first distillation column that receives a vapor stream from the flash vessel; a decanter that receives a first overhead stream from the first distillation column; an absorber, wherein a vapor stream received from the decanter is contacted with a solvent; and an acetaldehyde reactor that receives (1) a liquid bottoms stream comprising methyl iodide, acetaldehyde, and a portion of the solvent from the absorber and (2) optionally a polyol compound, wherein the acetaldehyde reactor comprises an acid catalyst to convert at least a portion of the acetaldehyde to an aldehyde derivative having a higher boiling point than acetaldehyde.

The above paragraphs present a simplified summary of the presently disclosed subject matter in order to provide a basic understanding of some aspects thereof. The summary is not an exhaustive overview, nor is it intended to identify key or critical elements to delineate the scope of the subject matter claimed below. Its sole purpose is to present some concepts in a simplified form as a prelude to the more detailed description set forth below.

BRIEF DESCRIPTION OF THE DRAWINGS

The claimed subject matter may be understood by reference to the following description taken in conjunction with the accompanying drawings, in which like reference numerals identify like elements, and in which:

While the disclosed process and system are susceptible to various modifications and alternative forms, the drawings illustrate specific embodiments herein described in detail by way of example. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

A detailed description of embodiments of the disclosed process follows. However, it is to be understood that the described embodiments are merely exemplary of the process and that the process may be embodied in various and alternative forms of the described embodiments. Therefore, specific procedural, structural and functional details which are addressed in the embodiments described herein are not to be interpreted as limiting, but merely as a basis for the claims and as a representative basis for teaching one skilled in the art to variously employ the disclosed process.

The designation of groups of the Periodic Table of the Elements as used herein is in accordance with the current IUPAC convention. The expression "HAc" is used herein as an abbreviation for acetaldehyde. The expression "MeI" is used herein as an abbreviation for methyl iodide. The expression "HI" is used herein as an abbreviation for hydrogen iodide. The expression "acac" is used herein as an abbreviation for acetoacetate anion, i.e., $H_3CC({=}O)CH_2C({=}O)O$—. Unless specifically indicated otherwise, the expression "wt %" as used herein refers to the percentage by weight of a particular component in the referenced composition. With respect to all ranges disclosed herein, such ranges are intended to include any combination of the mentioned upper and lower limits even if the particular combination is not specifically listed.

Embodiments of the disclosed process and system involve the production of acetic acid by carbonylating methanol in a carbonylation reaction. The carbonylation reaction may be represented by: $CH_3OH+CO\rightarrow CH_3COOH$ Embodiments of the disclosed process include: (a) obtaining HI in an acetic acid production system; and (b) continuously introducing a complexing agent into the system, wherein the complexing agent and HI interact to form a complex. The following description elaborates upon the disclosed process.

Acetic Acid Production

Figure 1:
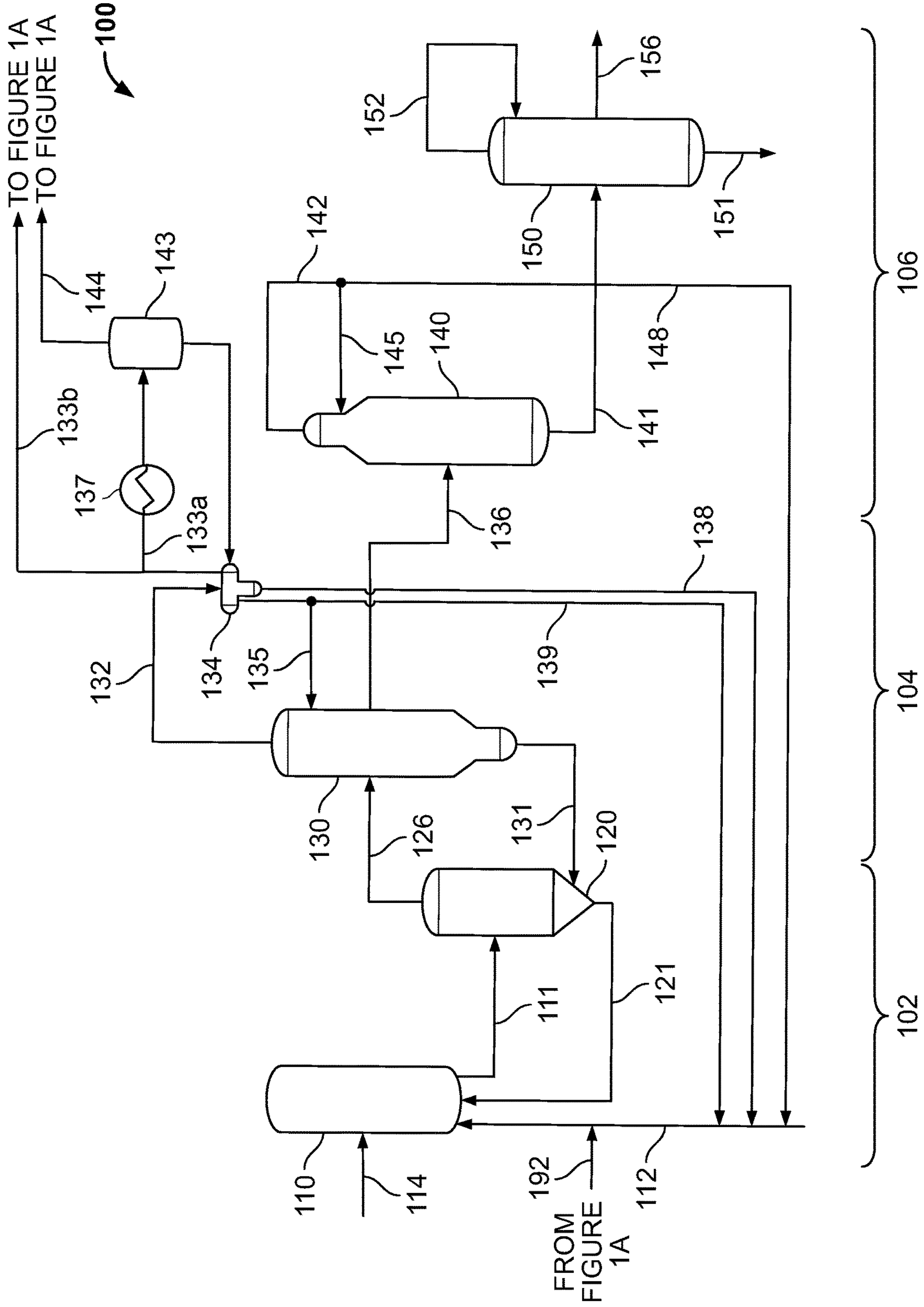
FIG. 1 is a schematic of an exemplary acetic acid production system in accordance with embodiments of the present techniques.

FIG. 1 is a schematic of an exemplary acetic acid production system 100 implementing the carbonylation reaction. In certain embodiments, the acetic acid system 100 may include a reaction area 102, a light-ends area 104, and a purification area 106. The reaction area 102 may include a reactor 110, a flash vessel 120, and associated equipment. The reactor 110 is a reactor or vessel in which methanol is carbonylated in the presence of a catalyst to form acetic acid at elevated pressure and temperature.

The flash vessel 120 is a tank or vessel in which a reaction mixture obtained in the reactor is at least partially depressurized and/or cooled to form a vapor stream and a liquid stream. The liquid stream 121 may be a product or composition which has components in the liquid state under the conditions of the processing step in which the stream is formed. The vapor stream 126 may be a product or composition which has components in the gaseous state under the conditions of the processing step in which the stream is formed.

The light-ends area 104 may include a separations column, for example a light-ends column 130, and associated equipment such as decanter 134. The light-ends column is a fractioning or distillation column and includes equipment associated with the column, such as heat exchangers, decanters, pumps, compressors, valves, and the like. The purification area 106 may include a drying column 140, optionally a heavy-ends column 150, and associated equipment, and so on. The heavy-ends column is a fractioning or distillation column and includes any equipment associated with the column, such as heat exchangers, decanters, pumps, compressors, valves, and the like. Further, as discussed below, various recycle streams may include streams 121, 138, 139, and 148. The recycle streams may be products or compositions recovered from a processing step downstream of the flash vessel 120 and which is recycled to the reactor 110, flash vessel 120, or light-ends column 130, and so forth.

In an embodiment, the reactor 110 may be configured to receive a carbon monoxide feed stream 114 and a methanol feed stream 112. A reaction mixture may be withdrawn from the reactor in stream 111. Other streams may be included such as, for example, a stream that may recycle a bottoms mixture of the reactor 110 back into the reactor 110, or a stream may be included to release a gas from the reactor 110.

In an embodiment, the flash vessel 120 may be configured to receive stream 111 from the reactor 110. In the flash vessel 120, stream 111 may be separated into a vapor stream 126 and a liquid stream 121. The vapor stream 126 may be communicated to the light-ends column 130, and the liquid stream 121 may be communicated to the reactor 110. In an embodiment, stream 126 may have acetic acid, water, methyl iodide, methyl acetate, HI, mixtures thereof and the like.

In an embodiment, the light-ends column 130 may be a distillation column and associated equipment such as a decanter 134, pumps, compressors, valves, and other related equipment. The light-ends column 130 may be configured to receive stream 126 from the flash vessel 120. In the illustrated embodiment, stream 132 is the overhead product from the light-ends column 130, and stream 131 is bottoms product from the light-ends column 130. As indicated, light-ends column 130 may include a decanter 134, and stream 132 may pass into decanter 134.

Stream 135 may emit from decanter 134 and recycle back to the light-ends column 130. Stream 138 may emit from decanter 134 and may recycle back to the reactor 110 via, for example, stream 112 or be combined with any of the other streams that feed the reactor. Stream 139 may recycle a portion of the light phase of decanter 134 back to the reactor 110 via, for example, stream 112. Stream 136 may emit from the light-ends column 130. Other streams may be included such as, for example, a stream that may recycle a bottoms mixture of the light-ends column 130 back into the light-ends column 130. Streams received by or emitted from the light-ends column 130 may pass through a pump, compressor, heat exchanger, and the like as is common in the art.

In an embodiment, the drying column 140 may be a vessel and associated equipment such as heat exchangers, decanters, pumps, compressors, valves, and the like. The drying column 140 may be configured to receive stream 136 from the light-ends column 130. The drying column 140 may separate components of stream 136 into streams 142 and 141. Stream 142 may emit from the drying column 140, recycle back to the drying column via stream 145, and/or recycle back to the reactor 110 through stream 148 (via, for example, stream 112). Stream 141 may emit from the drying column 140 and may include de-watered crude acetic acid product. Stream 142 may pass through equipment such as, for example, a heat exchanger or separation vessel before streams 145 or 148 recycle components of stream 142. Other streams may be included such as, for example, a stream may recycle a bottoms mixture of the drying column 140 back into the drying column 140. Streams received by or emitted from the drying column 140 may pass through a pump, compressor, heat exchanger, separation vessel, and the like as is common in the art.

The heavy-ends column 150 may be a distillation column and associated equipment such as heat exchangers, decanters, pumps, compressors, valves, and the like. The heavy-ends column 150 may be configured to receive stream 141 from the drying column 140. The heavy-ends column 150 may separate components from stream 141 into streams 151, 152, and 156. Streams 151 and 152 may be sent to additional processing equipment (not shown) for further processing. Stream 152 may also be recycled, for example, to light-ends column 130. Stream 156 may have acetic acid product.

A single column (not depicted) may be used in the place of the combination of the light-ends distillation column 130 and the drying column 140. The single column may vary in the diameter/height ratio and the number of stages according to the composition of vapor stream from the flash separation and the requisite product quality. For instance, U.S. Pat. No. 5,416,237, the teachings of which are incorporated herein by reference, discloses a single column distillation. Alternative embodiments for the acetic acid production system 100 may also be found in U.S. Pat. Nos. 6,552,221, 7,524,988, and 8,076,512, which are herein incorporated by reference.

In an embodiment, the carbonylation reaction in reactor 110 of system 100 may be performed in the presence of a catalyst. Catalysts may include, for example, rhodium catalysts and iridium catalysts.

Suitable rhodium catalysts are taught, for example, by U.S. Pat. No. 5,817,869, which is herein incorporated by reference. The rhodium catalysts may include rhodium metal and rhodium compounds. In an embodiment, the rhodium compounds may be selected from the group consisting of rhodium salts, rhodium oxides, rhodium acetates, organo-rhodium compounds, coordination compounds of rhodium, the like, and mixtures thereof in an embodiment, the rhodium compounds may be selected from the group consisting of $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, $[H]Rh(CO)_2I_2$, the like, and mixtures thereof. In an embodiment, the rhodium compounds may be selected from the group consisting of $[H]Rh(CO)_2I_2$, $Rh(CH_3CO_2)_2$, the like, and mixtures thereof.

Suitable iridium catalysts are taught, for example, by U.S. Pat. No. 5,932,764. The iridium catalysts may include iridium metal and iridium compounds. Examples of suitable iridium compounds include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]$—H+, $[Ir(CO)_2Br_2]$—H+, $[IR(CO)_2I_2]$—H+, $[Ir(CH_3)\ I_3\ (CO)_2]$—H+, $Ir_4\ (CO)I_2$, $IrCl_3{\cdot}4H_2O$, $IrBr_3{\cdot}4H_2O$, $Ir_3\ (CO)I_2$, $Ir_2O_3$, $IrO_2$, Ir(acac) $(CO)_2$, $Ir(acac)_3$, $Ir(OAc)_3$, $[Ir_3O(OAc)_6(H_2O)_3][OAc]$, $H_2[IrCl_6]$, the like, and mixtures thereof. In an embodiment, the iridium compounds may be selected from the group consisting of acetates, oxalates, acetoacetates, the like, and mixtures thereof. In an embodiment, the iridium compounds may be one or more acetates.

In an embodiment, the catalyst may be used with a co-catalyst. In an embodiment, co-catalysts may include metals and metal compounds selected from the group consisting of osmium, rhenium, ruthenium, cadmium, mercury, zinc, gallium, indium, and tungsten, their compounds, the like, and mixtures thereof. In an embodiment, co-catalysts may be selected from the group consisting of ruthenium compounds and osmium compounds. In an embodiment, co-catalysts may be one or more ruthenium compounds. In an embodiment, the co-catalysts may be one or more acetates.

The reaction rate depends upon the concentration of the catalyst in the reaction mixture in reactor 110. In an embodiment, the catalyst concentration may be in a range from about 1.0 mmol to about 100 mmol catalyst per liter (mmol/l) of reaction mixture. In some embodiments the catalyst concentration is at least 2.0 mmol/l, or at least 5.0 mmol/l, or at least 7.5 mmol/l. In some embodiments the catalyst concentration is at most 75 mmol/l, or at most 50 mmol/l, or at most 25 mmol/l. In particular embodiments, the catalyst concentration is from about 2.0 to about 75 mmol/l, or from about 5.0 to about 50 mmol/l, or from about 7.5 to about 25 mmol/l.

In an embodiment, the carbonylation reaction in reactor 110 of system 100 may be performed in the presence of a catalyst stabilizer. Suitable catalyst stabilizers include at least two types of catalyst stabilizers. The first type of catalyst stabilizer may be a metal iodide salt such as lithium iodide. The second type of catalyst stabilizer may be a non-salt stabilizer. In an embodiment, non-salt stabilizers may be pentavalent Group VA oxides, such as that disclosed in U.S. Pat. No. 9,790,159, which is herein incorporated by reference. In an embodiment, the catalyst stabilizer may be one or more phosphine oxides. In an embodiment, the catalyst may be CYTOP 503 from Solvay.

The one or more phosphine oxides, in one or more embodiments, are represented by the formula $R_3PO$, where R is alkyl or aryl, O is oxygen, P is phosphorous. In one or more embodiments, the one or more phosphine oxides include a compound mixture of at least four phosphine oxides, where each phosphine oxide has the formula $OPX_3$, wherein O is oxygen, P is phosphorous and X is independently selected from $C_4$-$C_{18}$ alkyls, $C_4$-$C_{18}$ aryls, $C_4$-$C_{18}$ cyclic alkyls, $C_4$-$C_{18}$ cyclic aryls and combinations thereof. Each phosphine oxide has at least 15, or at least 18 total carbon atoms.

Examples of suitable phosphine oxides for use in the compound mixture include, but are not limited to, tri-n-hexylphosphine oxide (THPO), tri-n-octylphosphine oxide (TOPO), tris(2,4,4-trimethylpentyl)-phosphine oxide, tricyclohexylphosphine oxide, tri-n-dodecylphosphine oxide, tri-n-octadecylphosphine oxide, tris(2-ethylhexyl)phosphine oxide, di-n-octylethylphosphine oxide, di-n-hexylisobutylphosphine oxide, octyldiisobutylphosphine oxide, tribenzylphosphine oxide, di-n-hexylbenzylphosphine oxide, di-n-octylbenzylphosphine oxide, 9-octyl-9-phosphabicyclo [3.3.1]nonane-9-oxide, dihexylmonooctylphosphine oxide, dioctylmonohexylphosphine oxide, dihexylmonodecylphosphine oxide, didecylmonohexylphosphine oxide, dioctylmonodecylphosphine oxide, didecylmonooctylphosphine oxide, and dihexylmonobutylphosphine oxide and the like.

The compound mixture includes from 1 wt % to 60 wt %, or from 35 wt % to 50 wt % of each phosphine oxide based on the total weight of compound mixture. In one or more specific, non-limiting embodiments, the compound mixture includes TOPO, THPO, dihexylmonooctylphosphine oxide and dioctylmonohexylphosphine oxide. For example, the compound mixture may include from 40 wt % to 44 wt % dioctylmonohexylphosphine oxide, from 28 wt % to 32 wt % dihexylmonooctylphosphine oxide, from 8 wt % to 16 wt % THPO and from 12 wt % to 16 wt % TOPO, for example.

In one or more embodiments, the compound mixture exhibits a melting point of less than 20° C., or less than 10° C., or less than 0° C., for example.

In one or more specific embodiments, the compound mixture is Cyanex™ 923, commercially available from Cytec Corporation.

The amount of pentavalent Group VA oxide, when used, is such that a ratio to rhodium is greater than about 60:1. In some embodiments, the ratio of the pentavalent Group 15 oxide to rhodium is from about 60:1 to about 500:1. In some embodiments, from about 0.1 to about 3 M of the pentavalent Group 15 oxide may be in the reaction mixture. In some embodiments, from about 0.15 to about 1.5 M, or from 0.25 to 1.2 M, of the pentavalent Group 15 oxide may be in the reaction mixture.

In other embodiments, the reaction may occur in the absence of a stabilizer selected from the group of metal iodide salts and non-metal stabilizers such as pentavalent Group 15 oxides. In further embodiments, the catalyst stabilizer may consist of a complexing agent which is brought into contact with the reaction mixture stream 111 in the flash vessel 120.

In an embodiment, hydrogen may also be fed into the reactor 110. Addition of hydrogen can enhance the carbonylation efficiency. In an embodiment, the concentration of hydrogen may be in a range of from about 0.1 mol % to about 5 mol % of carbon monoxide in the reactor 110. In an embodiment, the concentration of hydrogen may be in a range of from about 0.3 mol % to about 3 mol % of carbon monoxide in the reactor 110.

In an embodiment, the carbonylation reaction in reactor 110 of system 100 may be performed in the presence of water. In an embodiment, the concentration of water is from about 2 wt % to about 14 wt % based on the total weight of the reaction mixture. In an embodiment, the water concentration is from about 2 wt % to about 10 wt %. In an embodiment, the water concentration is from about 4 wt % to about 8 wt %.

In an embodiment, the carbonylation reaction may be performed in the presence of methyl acetate. Methyl acetate may be formed in situ. In embodiments, methyl acetate may be added as a starting material to the reaction mixture. In an embodiment, the concentration of methyl acetate may be from about 2 wt % to about 20 wt % based on the total weight of the reaction mixture. In an embodiment, the concentration of methyl acetate may be from about 2 wt % to about 16 wt %. In an embodiment, the concentration of methyl acetate may be from about 2 wt % to about 8 wt %. Alternatively, methyl acetate or a mixture of methyl acetate and methanol from byproduct streams of the methanolysis of polyvinyl acetate or ethylene-vinyl acetate copolymers can be used for the carbonylation reaction.

In an embodiment, the carbonylation reaction may be performed in the presence of methyl iodide. Methyl iodide may be a catalyst promoter. In an embodiment, the concentration of MeI may be from about 0.6 wt % to about 36 wt % based on the total weight of the reaction mixture. In an embodiment, the concentration of MeI may be from about 4 wt % to about 24 wt %. In an embodiment, the concentration of MeI may be from about 6 wt % to about 20 wt %. Alternatively, MeI may be generated in the reactor 110 by adding HI.

In an embodiment, methanol and carbon monoxide may be fed to the reactor 110 in stream 112 and stream 114, respectively. The methanol feed stream to the reactor 110 may come from a syngas-methanol facility or any other source. Methanol does not react directly with carbon monoxide to form acetic acid. It is converted to MeI by the HI present in the reactor 110 and then reacts with carbon monoxide and water to give acetic acid and regenerate the HI.

In an embodiment, the carbonylation reaction in reactor 110 of system 100 may occur at a temperature within the range of about 120° C. to about 250° C., alternatively, about 150° C. to about 250° C., alternatively, about 150° C. to about 200° C. In an embodiment, the carbonylation reaction in reactor 110 of system 100 may be performed under a pressure within the range of about 200 psia (1.38 MPa-a) to 2000 psia (13.8 MPa-a), alternatively, about 200 psia (1.38 MPa-a) to about 1,000 psia (6.9 MPa-a), alternatively, about 300 psia (2.1 MPa-a) to about 500 psia (3.4 MPa-a).

In an embodiment, the reaction mixture may be withdrawn from the reactor 110 through stream 111 and is flashed in flash vessel 120 to form a vapor stream 126 and a liquid stream 121. The reaction mixture in stream 111 may include acetic acid, methanol, methyl acetate, methyl iodide, acetaldehyde, carbon monoxide, carbon dioxide, water, HI, heavy impurities, catalyst, or combinations thereof. The flash vessel 120 may comprise any configuration for separating vapor and liquid components via a reduction in pressure. For example, the flash vessel 120 may comprise a flash tank, nozzle, valve, or combinations thereof.

The flash vessel 120 may have a pressure below that of the reactor 110. In an embodiment, the flash vessel 120 may have a pressure of from about 10 psig (69 kPa-g) to 100 psig (689 kPa-g). In an embodiment, the flash vessel 120 may have a temperature of from about 100° C. to 160° C.

The vapor stream 126 may include acetic acid and other volatile components such as methanol, methyl acetate, methyl iodide, carbon monoxide, carbon dioxide, water, entrained HI, complexed HI, and mixtures thereof. The liquid stream 121 may include the catalyst, complexed HI, HI, an azeotrope of HI and water, and mixtures thereof. The liquid stream 121 may further comprise sufficient amounts of water and acetic acid to carry and stabilize the catalyst, non-volatile catalyst stabilizers, or combinations thereof. The liquid stream 121 may recycle to the reactor 110. The vapor stream 126 may be communicated to light-ends column 130 for distillation.

In an embodiment, the vapor stream 126 may be distilled in a light-ends column 130 to form an overhead stream 132, a crude acetic acid product stream 136, and a bottom stream 131. In an embodiment, the light-ends column 130 may have at least 10 theoretical stages or 16 actual stages. In an alternative embodiment, the light-ends column 130 may have at least 14 theoretical stages. In an alternative embodiment, the light-ends column 130 may have at least 18 theoretical stages. In embodiments, one actual stage may equal approximately 0.6 theoretical stages. Actual stages can be trays or packing. The reaction mixture may be fed via stream 126 to the light-ends column 130 at the bottom or the first stage of the column 130.

Stream 132 may include acetaldehyde, water, carbon monoxide, carbon dioxide, methyl iodide, methyl acetate, methanol and acetic acid, and mixtures thereof. Stream 131 may have acetic acid, methyl iodide, methyl acetate, HI, water, and mixtures thereof. Stream 136 may have acetic acid, HI, water, heavy impurities, and mixtures thereof.

In an embodiment, the light-ends column 130 may be operated at an overhead pressure within the range of 20 psia (138 kPa-a) to 40 psia (276 kPa-a), alternatively, the overhead pressure may be within the range of 30 psia (207 kPa-a) to 35 psia (241 kPa-a). In an embodiment, the overhead temperature may be within the range of 95° C. to 135° C., alternatively, the overhead temperature may be within the range of 110° C. to 135° C., alternatively, the overhead temperature may be within the range of 125° C. to 135° C. In an embodiment, the light-ends column 130 may be operated at a bottom pressure within the range of 25 psia (172 kPa-a) to 45 psia (310 kPa-a), alternatively, the bottom pressure may be within the range of 30 psia (207 kPa-a) to 40 psia (276 kPa-a).

In an embodiment, the bottom temperature of the light-ends column 130 may be within the range of 115° C. to 155° C., alternatively, the bottom temperature is within the range of 125° C. to 135° C. In an embodiment, crude acetic acid in stream 136 may be emitted from the light-ends column 130 as a liquid side-draw. Stream 136 may be operated at a pressure within the range of 25 psia (172 kPa-a) to 45 psia (310 kPa-a), alternatively, the pressure may be within the range of 30 psia (207 kPa-a) to 40 psia (276 kPa-a). In an embodiment, the temperature of stream 136 may be within the range of 110° C. to 140° C., alternatively, the temperature may be within the range of 125° C. to 135° C. Stream 136 may be taken between the fifth to the eighth actual stage of the light-ends column 130.

In one or more embodiments, the crude acetic acid in stream 136 may be optionally subjected to further purification, such as, but not limited to, drying-distillation, in drying column 140 to remove water and heavy-ends distillation in stream 141. Stream 141 may be communicated to heavy-ends column 150 where heavy impurities such as propionic acid may be removed in stream 151 and final acetic acid product may be recovered in stream 156.

The overhead stream 132 from the light-ends column 130 may be condensed and decanted in a decanter 134 to form one or more liquid phase compositions, such as a light aqueous phase and a heavy organic phase, and a vapor phase composition. In some embodiments, a portion or all of the vapor phase may be sent as stream **133*b* or 144** for further processing, as discussed below.

In some embodiments, the vapor phase composition emitted from the decanter 134 comprises gases (primarily CO and $CO_2$), methyl iodide, light alkanes, acetaldehyde, acetic acid, or a combination thereof, flows via stream **133*a* to chiller 137. As used herein, "light alkanes" refers to linear and/or branched alkanes having six or less carbon atoms. In some embodiments, the vapor phase stream 133*a* may have a water concentration of less than 50 wt %, less than 40 wt %, or less than 30 wt %. In some embodiments, stream 133*a* may have Mel greater than 25%, greater than 35%, or greater than 45% by weight of the stream. In some embodiments, stream 133*a* flows through chiller 137 and knockout drum 143 to form stream 144. A portion of higher boiling material is removed from stream 133*a* in knockout drum 143. In some embodiments, vapor phase composition stream 144 may have a water concentration of less than 25 wt %, less than 15 wt %, or less than 5 wt %. In some embodiments, stream 144 may have methyl iodide greater than 30%, greater than 40%, or greater than 50% by weight of the stream. Make-up water may be introduced into the decanter 134** via a separate stream.

In some embodiments, rather than directing the vapor phase from decanter 134 via stream **133*a* to chiller 137 and knockout drum 143, the vapor phase may instead flow via stream 133*b* directly to acetaldehyde absorber 170. In such embodiments, the vapor phase composition emitted from the decanter 134 comprises gases (primarily CO and $CO_2$), methyl iodide, light alkanes, acetaldehyde, acetic acid, or a combination thereof. In some embodiments, the vapor phase stream 133*b* may have a water concentration of less than 50 wt %, less than 40 wt %, or less than 30 wt %. In some embodiments, stream 133*b* may have Mel greater than 25%, greater than 35%, or greater than 45% by weight of the stream. Although both 133*a* ands 133*b* are shown in FIG. 1, it is to be understood that stream 133*a* alone, stream 133*b*** alone, or a combination thereof may be present.

Streams **133*a*, 133*b* and/or 144 comprise a majority of the carbon monoxide and carbon dioxide from overhead stream 132. In some embodiments, a majority of the carbon monoxide and carbon dioxide means greater than or equal to 90 wt %, greater than or equal to 92 wt %, greater than or equal to 94 wt %, greater than or equal to 96 wt %, or greater than or equal to 98 wt %, of each carbon monoxide and carbon dioxide from overhead stream 132**.

Streams **133*a*, 133*b* and/or 144 comprise a minor portion of the acetaldehyde, methyl iodide, water, and acetic acid from overhead stream 132. In some embodiments, a minor portion of the acetaldehyde, methyl iodide, water, and acetic acid means less than or equal to 25 wt %, less than or equal to 20 wt %, less than or equal to 15 wt %, less than or equal to 10 wt %, or less than or equal to 5 wt %, of each acetaldehyde, methyl iodide, water, and acetic acid from overhead stream 132**.

Decanter Vapor Phase Absorption

Figure 1A:
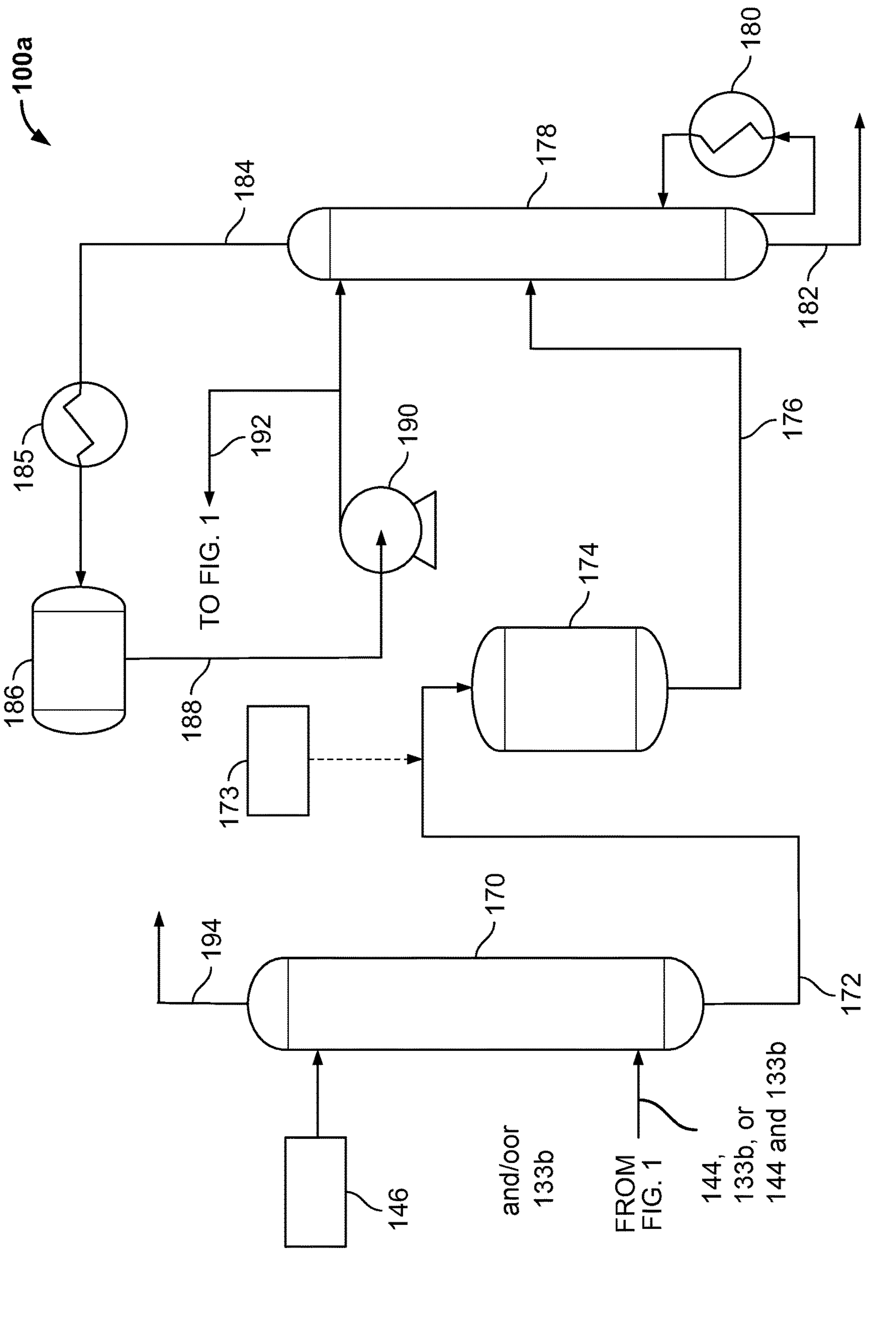
FIG. 1A is a schematic of an exemplary continuation of FIG. 1 in accordance with embodiments of the present techniques.

In some embodiments, as shown in FIG. 1A, at least a portion of the vapor phase from the decanter 134 is sent via stream **133*b* or 144 to an acetaldehyde absorber 170. In some embodiments, vapor streams 133*b* or 144 are contacted with a solvent 146 to absorb or remove acetaldehyde from streams 133*b* or 144**.

In some embodiments, the acetaldehyde absorber 170 can be operated at a temperature within the range of from 50° F. (10° C.) to 100° F. (38° C.), alternatively, within the range of from 60° F. (16° C.) to 80° F. (27° C.). In some embodiments, and a pressure within the range of 15 psia (103 kPa-a) to 35 psia (241 kPa-a), alternatively, the pressure may be within the range of 20 psia (138 kPa-a) to 30 psia (207 kPa-a).

Solvent 146 enters the upper portion of acetaldehyde absorber 170 and gas stream 133*b* or 144 enter the lower portion of acetaldehyde absorber 170. Acetaldehyde absorber 170 is sized and has dimensions, and optionally internals, to promote contact between gas stream 133*b* or 144 and solvent 146 for a time sufficient to absorb or remove acetaldehyde from gas stream 133*b* or 144. Streams received by or emitted from the acetaldehyde absorber 170 may pass through a pump, compressor, heat exchanger, separation vessel, and the like as is common in the art.

In some embodiments, the solvent is an acetate compound, a hydroxyl compound, or a combination thereof. In some embodiments, the acetate compound has one or both of a single acetate group and a boiling point in the range of from 45° C. to 79° C., or in the range of from 50° C. to 70° C. In some embodiments, the acetate compound is methyl acetate. In some embodiments, the hydroxyl compound has one or both of a single hydroxyl group and a boiling point in the range of from 45° C. to 79° C., or in the range of from 50° C. to 70° C. In some embodiments, the hydroxyl compound is methyl alcohol.

Effluent from the acetaldehyde absorber 170 include overhead vapor stream 194 and bottoms stream 172. In some embodiments, absorber overhead stream 194 is further processed prior to removal from the acetic acid system 100. In some embodiments, absorber bottoms stream 172 flows to acetaldehyde reactor 174, optionally, in combination with a polyol compound 173.

It should be noted that removal of the troublesome byproduct acetaldehyde from the acetic acid system 100 via physical or chemical techniques has occupied significant research time in the art for over a decade. This problematic byproduct and its aldehyde derivatives may unfortunately impact product purity. The acetaldehyde may also serve undesirably as a precursor to various hydrocarbons which impact decanter 134 heavy density, and as a precursor to higher alkyl iodides which may require expensive adsorption beds for their removal, for example.

In some embodiments, the solvent also functions to remove methyl iodide from the decanter vapor phase composition streams 133*b* or 144. This provides an additional method for recovery of methyl iodide through subsystem 100*a*, wherein the methyl iodide is recycled to the acetic acid system 100 via stream 192. In some embodiments, the methyl iodide is sent to acetic acid production reactor 110.

Absorber bottoms stream 172 comprises a majority of the methyl iodide from vapor phase composition stream 133*b* or 144. In some embodiments, a majority of the methyl iodide means greater than or equal to 50 wt %, greater than or equal to 60 wt %, greater than or equal to 70 wt %, greater than or equal to 80 wt %, or greater than or equal to 90 wt %, of the methyl iodide from vapor phase composition stream 133 or 144.

Conversion of Acetaldehyde

According to the present techniques, acetaldehyde may be removed from the acetic acid system 100 by providing a stream comprising acetaldehyde from the acetic acid system 100 and contacting the stream (e.g., 172, which may optionally include polyol compound 173) with an acid catalyst. Upon contacting the stream 172 with the acid catalyst in acetaldehyde reactor 174, at least a portion of the acetaldehyde in the stream is converted to an aldehyde derivative having a boiling point greater than the boiling point of acetaldehyde.

Without wishing to be bound by any particular theory, in acetaldehyde reactor 174, it is believed that acetaldehyde undergoes rapid acid catalyzed oligomerization to form paraldehyde in an equilibrium reaction which goes to about 75% completion, for example, depending on operating conditions in the acetaldehyde reactor 174. Paraldehyde has a boiling point of 124° C. and thus would be a good candidate for separation from MeI by distillation. However, paraldehyde decomposes (back to acetaldehyde) upon heating to about 60° C., for instance, and thus while paraldehyde may be the kinetically-favored product of acid catalysis, it is not very stable. Therefore, paraldehyde may not be a suitable candidate in a downstream distillation for separation from MeI.

However, if the initial and rapidly formed paraldehyde is left in contact with the acid catalyst, the paraldehyde generally converts to the thermodynamically-favored crotonaldehyde. This is likely not a direct paraldehyde to crotonaldehyde conversion but rather occurs via paraldehyde reversion to acetaldehyde followed by aldol condensation in which two molecules of acetaldehyde react together to form crotonaldehyde. Crotonaldehyde has a boiling point of 102° C. and thus is another candidate to separate from the low boiling methyl iodide. Unlike paraldehyde, however, crotonaldehyde does not generally decompose to lower boiling compounds upon heating over modest temperatures and times. Acid catalyst or resin concentration and conditions may be tailored to facilitate the thermodynamically-favored crotonaldehyde to be formed rapidly and quantitatively.

In some embodiments, the acid catalyst can be strongly acidic ion-exchange resins. As used herein, "strongly acidic" or "strong acid" refers to an acid that completely ionizes in water, including, but not limited to, hydrochloric acid, hydrobromic acid, hydroiodic acid ("HI"), sulfuric acid, nitric acid, chloric acid, and perchloric acid. Strong acids can further include mineral acids, sulfonic acids (such as para-toluene sulfonic acid and methanesulfonic acid), heteropolyacids (such as tungstosilic acid, phosphotungstic acid and phosphomolybdic acid), and any of these acids when bound to a matrix (such as Amberlyst™ 15 (available from Sigma Aldrich, St. Louis, Missouri), which is a resin with bound sulfonic acid groups). In one instance, the ion-exchange resin, such as those that may be employed in acetaldehyde reactor 182, include strongly acidic ion-exchange resins, for example, such as Amberlyst™ 15Dry. Amberlyst™ 15Dry, a strongly acidic cation exchange resin consisting of a sulfonic acid functionalized co-polymer of styrene and divinylbenzene, may be manufactured as opaque beads and may have a macroreticular pore structure with hydrogen ion sites located throughout each bead. The surface area may be about 53 $m^2/g$, the average pore diameter may be about 300 Angstroms, and the total pore volume may be about 0.40 cc/g. Amberlyst™ 15Dry may be utilized in essentially non-aqueous systems (e.g., less than 5 wt % water). Therefore, the reactive feed stream may be essentially or substantially nonaqueous with use of Amberlyst™ 15Dry.

In some embodiments, contacting the reactive feed stream, comprising absorber bottoms stream 172 and optionally a polyol compound, with the ion-exchange resin (e.g., in acetaldehyde reactor 174) may occur at room temperature, ambient temperature, or a temperature below the boiling point of acetaldehyde, and so on. In an embodiment, contacting the solution with the ion-exchange resin may occur for at least about 30 minutes. The mass ratio of aldehyde to ion-exchange resin may be in a range of about 0.1 to about 2.0, for example.

In some embodiments, feed stream 172 to acetaldehyde reactor 174 further include a metered stream of a hydroxyl compound 173. Suitable hydroxyl compounds for reacting with the aldehydes include alcohols, glycols, and polyols. Suitable alcohols include $C_4$ to $C_{10}$ alcohols. In some embodiments, sterically bulky alcohols, such as 2-ethylhexan-1-ol, 2-methylhexan-2-ol, 3-methylpentan-3-ol, 2-methylpentan-2-ol, 3-methyl-2-butanol, 2-methylbutan-2-ol, and 3-methyl-2-butanol, are used. As used herein, "glycol," means any compound that has two hydroxyl groups. Suitable glycols include ethylene glycol, propylene glycol, 1,4-butanediol, 1,3-butanediol, 1,5-pentanediol, 1,6-hexanediol, 2-methyl-1,3-propanediol, 2,2-dimethyl-1,3-propanediol, cyclohexane-1,4-dimethanol, and neopentyl glycol, the like, and mixtures thereof. Suitable polyols include those which have three or more hydroxyl functional groups such as glycerin. In some embodiments, glycols are selected because they form stable cyclic acetals with aldehydes. In some embodiments, ethylene glycol is selected because it is inexpensive and readily available.

In some embodiments, the hydroxyl compound is used in an amount within the range of 1 molar equivalent to 10 or 2 molar equivalents to 5 molar equivalents of the acetaldehyde. Use of the hydroxyl compound in combination with stream 172 at 1 molar equivalent or more results in conversion of all or substantially all (e.g., greater than or equal to 90 wt % or greater than or equal to 95 wt %) of the acetaldehyde in stream 172 to acetal.

In some embodiments, the hydroxyl compound is used in an amount less than 1 molar equivalent the acetaldehyde impurities. Use of the hydroxyl compound in combination with stream 172 at less than 1 molar equivalent results in partial conversion of the acetaldehyde in stream 172 to acetal while all or substantially all (e.g., greater than or equal to 90 wt % or greater than or equal to 95 wt %) of the remaining acetaldehyde is converted to crotonaldehyde.

In some embodiments, the acetaldehyde absorber bottoms stream 172 is contacted with the acid catalyst in acetaldehyde reactor 174, and hence the conversion of a portion of the acetaldehyde in acetaldehyde absorber bottoms stream 172, occurs at a temperature in the range of from 20° C. to 135° C., or 20° C. to 50° C.

In some embodiments, the acetaldehyde absorber bottoms stream 172 is contacted with the acid catalyst in acetaldehyde reactor 174, and hence the absorption of a portion of the acetaldehyde in acetaldehyde absorber bottoms stream 172, occurs at a pressure in the range of from 14.7 psia (101 kPa-a) to 263 psia (1,813 kPa-a), or 14.7 psia (101 kPa-a) to 40 psia (276 kPa-a). In some embodiments, the pressure in acetaldehyde reactor 174 is greater than or equal to the vapor pressure of acetaldehyde at the temperature in acetaldehyde reactor 174.

In some embodiments, when a hydroxyl compound 173 is not added to the reactive feed stream to acetaldehyde reactor 174, effluent stream 176 from acetaldehyde reactor 174 comprises crotonaldehyde in place of all, substantially all, or a portion of the acetaldehyde in feed stream 172 to acetaldehyde reactor 174.

In some embodiments, when a hydroxyl compound 173 is added at a rate of one or more molar equivalents of the acetaldehyde in the feed stream 172 to acetaldehyde reactor 174, effluent stream 176 from acetaldehyde reactor 174 comprises acetal in place of all, substantially all, or a portion of the acetaldehyde in feed stream 172 to acetaldehyde reactor 174.

In some embodiments, when a hydroxyl compound 173 is added at a rate of less than one molar equivalent of the acetaldehyde in the feed stream 172 to acetaldehyde reactor 174, effluent stream 176 from acetaldehyde reactor 174 comprises a mixture of acetal and crotonaldehyde in place of all, substantially all, or a portion of the acetaldehyde in feed stream 172 to acetaldehyde reactor 174.

In one or more embodiments, the disclosed process may be performed in a continuous format. For example, two resin beds or two acetaldehyde reactors 174 may be disposed in parallel, and while one is being regenerated, the other is in operation. On the other hand, the disclosed process may be performed in a batch format. The acetaldehyde reactor 174 may be in continuous or batch operation and may include a tank of dimension and material suitable for production of acetic acid. Streams received by or emitted from the acetaldehyde reactor 174 may pass through a pump, compressor, heat exchanger, separation vessel, and the like as is common in the art.

Acetaldehyde Reactor Effluent Distillation

In some embodiments, as shown in FIG. 1A, the effluent stream 176 from the acetaldehyde reactor 174 is sent to a reactor effluent distillation column 178. The reactor effluent distillation column is a fractioning or distillation column and includes equipment associated with the column, such as heat exchangers, decanters, pumps, compressors, valves, and the like. In reactor effluent distillation column 178, the aldehyde derivative is separated from lower boiling components, such as, but not limited to methyl iodide, methyl acetate, and water. In one example of a reactor effluent distillation column 178, the stream 176 is distilled to form a vapor overhead stream 184, comprising methyl iodide, methyl acetate, light alkanes, acetaldehyde, and water, and a bottoms stream 182, comprising a portion of the solvent and all or substantially all (e.g., greater than or equal to 90 wt % or greater than or equal to 95 wt %) of the aldehyde derivative from the effluent stream 176 from acetaldehyde reactor 174, wherein the aldehyde derivative is crotonaldehyde, acetal, or a combination thereof.

In some embodiments, the overhead temperature of the distillation in the reactor effluent distillation column 178 is in the range of about 140° F. (60° C.) to about 200° F. (93° C.), about 150° F. (66° C.) to about 190° F. (88° C.), or 160° F. (71° C.) to about 180° F. (82° C.). In particular examples, the overhead vapor stream 184 can be operated at a pressure within the range of 5 psig (34 kPa-g) to 35 psig (241 kPa-g), 10 psig (69 kPa-g) to 30 psig (207 kPa-g), or 15 psig (103 kPa-g) to 25 psig (172 kPa-g). Lowering the overhead temperature of the reactor effluent distillation column 178 desirably assures that all or substantially all (e.g., greater than or equal to 90 wt % or greater than or equal to 95 wt %) aldehyde derivative will be concentrated in the bottoms stream 182.

In some embodiments, the bottom temperature of the distillation in the reactor effluent distillation column 178 is in the range of about 185° F. (85° C.) to about 245° F. (118° C.), about 195° F. (91° C.) to about 235° F. (113° C.), or 205° F. (96° C.) to about 225° F. (107° C.). In particular examples, the bottoms stream 182 can be operated at a pressure within the range of 5 psig (34 kPa-g) to 35 psig (241 kPa-g), 10 psig (103 kPa-g) to 30 psig (207 kPa-g), or 15 psig (103 kPa-g) to 25 psig (172 kPa-g). According to certain embodiments, the heat input to column 178 is provided by reboiler 180. The bottoms stream 182 from reactor effluent distillation column 178 is sent to a waste disposition or otherwise removed from acetic acid system 100.

The overhead stream 184 from acetaldehyde reactor effluent distillation column 178 is recycled as reflux to effluent distillation column 178, recycled to acetic acid system 100 as stream 192, or a combination thereof. In some embodiments, stream 192 is sent to the acetic acid production reactor 110. Streams received by or emitted from reactor effluent distillation column 178 may pass through a pump, compressor, heat exchanger, and the like as is common in the art.

SUMMARY

In some aspects, methods for removing acetaldehyde from an acetic acid system are disclosed. In an embodiment, a method comprises providing from the acetic acid system a light-ends stream, comprising carbon monoxide, carbon dioxide, acetaldehyde, methyl iodide, methyl acetate, methanol, water, acetic acid, or mixtures thereof, and condensing the light-ends stream to form one or more liquid phase compositions and a vapor phase composition. The one or more liquid phase compositions comprise a majority of the water and acetic acid, and the vapor phase composition comprises a majority of the carbon monoxide and carbon dioxide and a minor portion of the acetaldehyde, methyl iodide, water, and acetic acid. The vapor phase composition is contacted with a solvent in an absorber to produce an absorber overhead vapor stream and an absorber bottoms liquid stream, wherein the absorber overhead vapor stream comprises carbon monoxide, carbon dioxide, and a first portion of the solvent, and the absorber bottoms liquid stream comprises methyl iodide, acetaldehyde, and a second portion of the solvent; and contacting a reactive feed stream, comprising the absorber bottoms liquid stream, and optionally a polyol compound, with an acid catalyst to form a reacted stream comprising an aldehyde derivative, wherein the aldehyde derivative is formed by conversion of at least a portion of the acetaldehyde and has a higher boiling point than acetaldehyde.

The vapor phase composition is contacted with a solvent in an absorber to produce an absorber overhead vapor stream and a liquid bottoms stream. The absorber overhead vapor stream comprises carbon monoxide, carbon dioxide, and a first portion of the solvent, and the absorber bottoms liquid stream comprises methyl iodide, acetaldehyde, and a second portion of the solvent. A reactive feed stream, comprising the absorber bottoms liquid stream, and optionally a polyol compound, is contacted with an acid catalyst to form a reacted stream, wherein contacting the reactive feed stream with the acid catalyst converts at least a portion of the acetaldehyde to an aldehyde derivative having a higher boiling point than acetaldehyde.

In some embodiments, in addition to the foregoing steps of the method for removing acetaldehyde from an acetic acid system, the method further comprises removing the aldehyde derivative from the reacted stream. The removal method can include distilling the reacted stream to form a distillation overhead stream and a distillation bottoms stream, wherein the distillation bottoms stream comprises a portion of the aldehyde derivative. The distillation bottoms stream can then be discharged from the acetic acid system.

In some embodiments, in addition to the foregoing steps of the method for removing acetaldehyde from an acetic acid system, the method further comprises recycling the distillation overhead stream within the acetic acid system. In some instances, the acetic acid system comprises an acetic acid production reactor and an acetaldehyde reactor, and the distillation overhead stream is recycled to the acetic acid production reactor, the acetaldehyde reactor effluent distillation column, or a combination thereof.

In some embodiments, in addition to the foregoing steps of the method for removing acetaldehyde from an acetic acid system, the method further comprises condensing a portion of the water and acetic acid in the vapor phase composition to form a condensed portion of the vapor phase composition and removing the condensed portion from the vapor phase composition. In some embodiments, the vapor phase composition may flow through a chiller to condense at least a portion of the water and acetic acid, and the condensed portion is then removed from the vapor phase composition in a knockout drum.

In other embodiments, in addition to the foregoing steps of the method for removing acetaldehyde from an acetic acid system, the method further comprises any one or any combination of the following:

(a) the aldehyde derivative is crotonaldehyde, acetal, or a combination thereof;

(b) the hydroxyl compound: i) comprises a $C_2$-$C_{10}$ diol or triol; ii) is selected from the group consisting of ethylene glycol, propylene glycol, 1,4-butanediol, 1,3-butanediol, 1,3-propanediol, 2-methyl-1,3-propanediol, 2,2-dimethyl-1,3-propanediol, cyclohexane-1,4-dimethanol, glycerin, and combinations thereof; or is selected from the group consisting of 1,3-propanediol, 2-methyl-1,3-propanediol, glycerin, and combinations thereof;

(c) the vapor phase composition exiting the decanter comprises less than 1 wt % acetic acid;

(d) the acetic acid system comprises an acetaldehyde reactor having a fixed bed comprising the acid catalyst, and the reactive feed stream is fed to the acetaldehyde reactor; and (e) the acid catalyst is an acidic ion exchange resin.

In some aspects, methods for producing acetic acid are disclosed. In an embodiment, a method for producing acetic acid comprises:

(a) reacting methanol and carbon monoxide in the presence of a carbonylation catalyst to form acetic acid in an acetic acid production reactor;

(b) flashing a reaction mixture discharged from the acetic acid production reactor into a vapor stream and a liquid stream, the vapor stream comprising acetic acid, methyl iodide, and acetaldehyde;

(c) separating the vapor stream by distillation in a first distillation column into: (1) a product side stream comprising acetic acid and water; (2) a first bottoms stream; and (3) a first overhead stream comprising carbon monoxide, carbon dioxide, acetaldehyde, methyl iodide, methyl acetate, methanol, water, acetic acid, or mixtures thereof;

(d) condensing the first overhead stream to form: (1) one or more liquid phase streams, comprising a majority of the water and acetic acid; and (2) a vapor phase composition, comprising a majority of the carbon monoxide and carbon dioxide and a minor portion of the acetaldehyde, methyl iodide, water, and acetic acid;

(e) contacting the vapor phase composition with a solvent to produce a treated liquid stream, comprising methyl iodide, acetaldehyde, and a portion of the solvent; and (f) contacting a reactive feed stream, comprising the treated liquid stream, and optionally a polyol compound, with an acid catalyst to form a reacted stream, wherein contacting the reactive feed stream with the acid catalyst converts at least a portion of the acetaldehyde to an aldehyde derivative having a higher boiling point than acetaldehyde.

In some embodiments, in addition to the foregoing steps of the method for producing acetic acid, the method further comprises removing the aldehyde derivative from the reacted stream. The removal method can include distilling the reacted stream to form a distillation overhead stream and a distillation bottoms stream, wherein the distillation bottoms stream comprises a portion of the aldehyde derivative. The distillation bottoms stream can then be discharged from the acetic acid system.

In some embodiments, in addition to the foregoing steps of the method for producing acetic acid, the method further comprises recycling the distillation overhead stream within the acetic acid system. In some instances, the acetic acid system comprises an acetic acid production reactor and an acetaldehyde reactor, and the distillation overhead stream is recycled to the acetic acid production reactor, the acetaldehyde reactor effluent distillation column, or a combination thereof.

In some embodiments, in addition to the foregoing steps of the methods for producing acetic acid, the method further comprises condensing a portion of the water and acetic acid in the vapor phase composition to form a condensed portion of the vapor phase composition and removing the condensed portion from the vapor phase composition. In some embodiments, the vapor phase composition may flow through a chiller to condense at least a portion of the water and acetic acid, and the condensed portion is then removed from the vapor phase composition in a knockout drum.

In other embodiments, in addition to the foregoing steps of the method for producing acetic acid, the method further comprises any one or any combination of the following:

(a) the aldehyde derivative is crotonaldehyde, acetal, or a combination thereof;

(b) the hydroxyl compound: i) comprises a $C_2$-$C_{10}$ diol or triol; ii) is selected from the group consisting of ethylene glycol, propylene glycol, 1,4-butanediol, 1,3-butanediol, 1,3-propanediol, 2-methyl-1,3-propanediol, 2,2-dimethyl-1,3-propanediol, cyclohexane-1,4-dimethanol, glycerin, and combinations thereof; or is selected from the group consisting of 1,3-propanediol, 2-methyl-1,3-propanediol, glycerin, and combinations thereof;

(c) the vapor phase composition comprises less than 1 wt % acetic acid;

(d) the acetic acid system comprises an acetaldehyde reactor having a fixed bed comprising the acid catalyst, and the reactive feed stream is fed to the acetaldehyde reactor; and (e) the acid catalyst is an acidic ion exchange resin.

In some aspects, acetic acid production systems are disclosed. In an embodiment, an acetic acid production system comprises:

(a) an acetic acid production reactor to react methanol and carbon monoxide in the presence of a carbonylation catalyst to form acetic acid;

(b) a flash vessel that receives a reaction mixture comprising the acetic acid from the reactor;

(c) a first distillation column that receives a vapor stream from the flash vessel;

(d) a decanter that receives a condensed first overhead stream from the first distillation column;

(e) an absorber wherein a vapor phase stream received from the decanter is contacted with a solvent; and (f) an acetaldehyde reactor that receives (1) a liquid bottoms stream comprising methyl iodide, acetaldehyde, and a portion of the solvent from the absorber and (2) optionally a polyol compound, wherein the acetaldehyde reactor comprises an acid catalyst to convert at least a portion of the acetaldehyde to an aldehyde derivative having a higher boiling point than acetaldehyde.

In other embodiments, in addition to the foregoing elements of an acetic acid production system, the system comprises any one or any combination of the following:

(a) a chiller and knock-out drum, wherein at least a portion of the water and acetic acid in the vapor phase composition is condensed in the chiller, and the condensed water and acetic acid are removed from the vapor phase composition in the knock-out;

(b) a second distillation column that receives an effluent from the acetaldehyde reactor.

In other embodiments, in addition to the foregoing elements of an acetic acid production system, the system comprises any one or any combination of the following:

(a) the aldehyde derivative is crotonaldehyde, acetal, or a combination thereof; and (b) the acid catalyst is an acidic ion exchange resin.

Although the disclosed process and system have been described in detail, it should be understood that various changes, substitutions and alterations can be made herein without departing from the spirit and scope of the invention as defined by the appended claims. Moreover, the scope of the present application is not intended to be limited to the particular embodiments of the processes, machines, compositions, means, methods, and/or steps described in the specification. As one of the ordinary skill in the art will readily appreciate from the present disclosure, processes, machines, compositions, means, methods, and/or steps, presently existing or later to be developed that perform substantially the same function or achieve substantially the same result as the corresponding embodiments described herein, may be utilized according to the present invention. Accordingly, the appended claims are intended to include within their scope such processes, machines, compositions, means, methods, and/or steps.

EXAMPLES

The following investigations and examples are intended to be illustrative only, and are not intended to be, nor should they be construed as, limiting the scope of the present invention in any way.

Process Modeling

Test Methods

In Example 1, an Aspen computer simulation (ASPEN Plus V10 steady-state simulation) of process streams and conditions was used to simulate embodiments of the invention. The simulated process flow diagram ("PFD") is shown in FIG. 1A. Flow rates in the example are shown on a normalized parts-per-hundred (pph) basis, wherein the feed rate (144) into FIG. 1A is 100 parts.

Example 1

Example 1 demonstrates an embodiment wherein the solvent 146 is methyl acetate ("MeAc") and no polyol compound 173 is added to the absorber liquid bottoms stream 172. Amberlyst 15 is used as the acid catalyst in acetaldehyde reactor 174. In this PFD, the absorber 170 operates with an overhead temperature of about 93° F. (34° C.), a bottoms temperature of about 85° F. (29° C.), and overhead and bottoms pressure of about 18 psig (124 kPa-g). Process conditions and compositions for streams 144, 146, 172, 182, 184, 192, and 194 are shown in TABLE 1, below.

TABLE 1 shows the calculated concentration (wt %) of gases (primarily CO and $CO_2$), acetaldehyde ("HAc"), methyl iodide ("MeI"), light alkanes ("LA"), methyl acetate ("MeAc"), water ("$H_2O$"), crotonaldehyde ("CA"), and acetic acid ("GAA") in each identified stream. The mass balance in TABLE 1 indicates 0.65 parts of HAc entering acetaldehyde absorber 170 in gas stream 144 and 0.44 parts of CA exiting system 100*a* in the bottoms stream 182 from reactor effluent distillation column 178. Since 1 part by weight of CA equates to 1.26 parts by weight of HAc, 0.44 parts by weight of CA accounts for 0.55 parts by weight of HAc removed from system 100*a* such that about 85% of the incoming HAc is removed by system 100*a*.

TABLE 1

| | Stream | | | | | | |
|---|---|---|---|---|---|---|---|
| Stream Attribute | 144 | 146 | 172 | 182 | 184 | 192 | 194 |
| Flow (100 part basis) | 100 | 92.2 | 123.6 | 0.878 | 245 | 122.7 | 68.6 |
| Temp. (° F.) | 70 | 70 | 85 | 214 | 170 | 84 | 93 |
| Temp. (° C.) | 21 | 21 | 29 | 101 | 77 | 29 | 34 |
| Pressure (psig) | 18 | 18 | 18 | 20 | 20 | 20 | 18 |
| Pressure (kPa-g) | 124 | 124 | 124 | 138 | 138 | 138 | 124 |
| Gases (wt %) | 43.7 | 0.0 | 1.0 | 0.0 | 1.0 | 1.0 | 61.9 |
| HAc (wt %) | 0.65 | 0.0 | 0.5 | 0.0 | 0.1 | 0.1 | 0.0 |
| MeI (wt %) | 50.2 | 0.0 | 40.6 | 0.0 | 40.9 | 40.9 | 0.1 |
| LA (wt %) | 3.8 | 0.0 | 2.9 | 0.0 | 2.9 | 2.9 | 0.3 |
| MeAc (wt %) | 0.8 | 100.0 | 54.3 | 49.8 | 54.4 | 54.4 | 37.7 |
| $H_2O$ (wt %) | 0.7 | 0.0 | 0.6 | 0.0 | 0.7 | 0.7 | 0.0 |
| CA (wt %) | 0.0 | 0.0 | 0.0 | 50.0 | 0.0 | 0.0 | 0.0 |
| GAA (wt %) | 0.0 | 0.0 | 0.0 | 0.1 | 0.0 | 0.0 | 0.0 |

In Example 1, acetaldehyde reactor effluent distillation column 178 was simulated with 16 theoretical stages, and the acetaldehyde absorber 170 was simulated with 20 theoretical stages. Normalized heat input to reboiler 180 was 7.27 MMBTU per 100 lb (16.9 GJ per kg) acetaldehyde removal. One of the ordinary skill in the art will readily determine actual column sizing based on this disclosure, a desired feed rate to acetaldehyde reactor effluent distillation column 178, and a desired acetaldehyde removal rate.

Static Slurry Experiments

Test Methods

In Examples 2-7 and 13, infrared spectra were collected on a Nicolet 6700 FTIR spectrometer obtained from Thermo Scientific. The spectrometer was equipped with a Smart Miracle accessory also obtained from Thermo Scientific. The accessory contained a 3 bounce, zinc selenide ATR crystal. Those skilled in the art of infrared spectroscopy will realize that use of such an accessory will allow infrared absorbance peaks of HAc (1733 $cm^{-1}$), crotonaldehyde (1702 $cm^{-1}$), and paraldehyde (1342 cm 1 and 856 $cm^{-1}$), to be monitored and quantified. Examples 1-5 address static slurries or mixtures. Example 6 addresses a flow-through bed mode. FTIR absorbance values were converted to molar values based on standards in the 0-1M range prepared separately for each of acetaldehyde, crotonaldehyde and paraldehyde in decane.

Raw Materials

Raw materials used herein are shown in Table 1, below. All starting materials are available from Sigma Aldrich, St. Louis, Missouri.

TABLE 2

| Label | Composition*** | Type/Grade |
|---|---|---|
| MeOH | Methyl alcohol | — |
| MeAc | Methyl acetate | — |
| A15 | Amberlyst ™ 15 Dry. | 200-400 um particle size, <1.6% moisture |
| — | Amberlite CG-50 ™ | weak acid resin |
| — | Zeolite 45871 HY ™ (from Alfa Aesar) | acidic zeolite |

Examples 2-4

Figure 2:
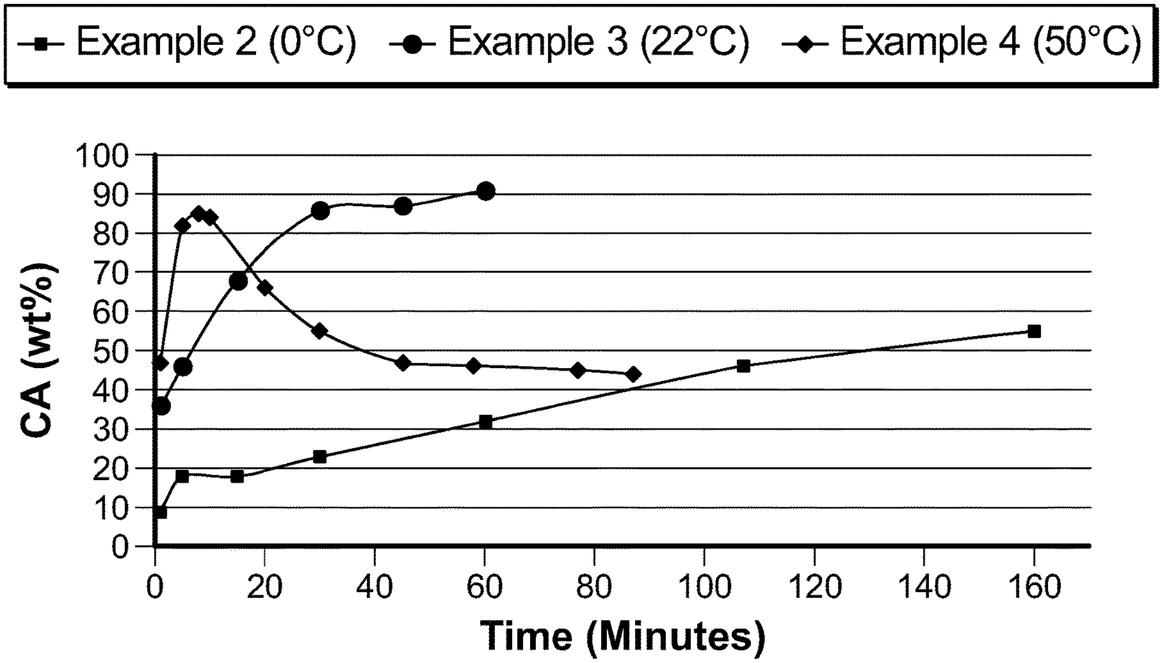
FIG. 2 is an overlaid graph of % crotonaldehyde vs. time for different reaction temperatures in accordance with embodiments of the present techniques.

Mixtures of 0.07 g A15 and 3 ml of a HAc solution (1.6 M concentration in MeAc) were added to vials. In Examples 2-4, vials were then slurried and stirred at 0° C., 22° C., and 50° C., respectively, and each was periodically sampled. The vials were septum sealed in order to prevent volatilization of acetaldehyde and stirred in order to optimize contact between solution and A15. TABLE 3 and FIG. 2 show how the rate of CA formation can be controlled by varying temperature. Example 2 shows that at 0° C., there is a steady increase in the amount of CA to a peak value of 54 wt % at 160 minutes. Example 3 shows that at 22° C., the rate of increase is significantly greater than Example 2, reaching a peak value of 90 wt % at 60 minutes. Example 4 shows that at 50° C., the rate of increase is much greater than Example 3, reaching a peak value of approximately 90 wt % in less than 20 minutes. Without wishing to be bound by any particular theory, it is believed, based on previously observed behavior of A15, as described in U.S. Pat. No. 8,969,613, fully incorporated by reference herein, TABLE 3 and FIG. 2 are believed to show that HAc was rapidly trimerized to paraldehyde ("PLD"), followed by less rapid formation of CA crotonaldehyde. After CA formation, a portion of the CA is adsorbed onto the A15. This explains the decrease in CA after 20 minutes at 55° C., where CA formation peaked quickly, followed by adsorption of the CA onto the A15. It is believed that all three temperatures would have reached an equilibrium amount of CA in solution and CA adsorbed onto A15 if the testing had continued for a longer time period. However, these samples show that CA formation rate is responsive to increases in temperature.

TABLE 3

| | | Weight Percent CA | | |
|---|---|---|---|---|
| Example | | 2 | 3 | 4 |
| Temp. (° C.) | | 0 | 22 | 50 |
| Time (min.) | 1 | 9 | 36 | 47 |
| | 5 | 18 | 46 | 82 |
| | 8 | — | — | 85 |
| | 10 | — | — | 84 |
| | 15 | 18 | 68 | — |
| | 20 | — | — | 66 |
| | 30 | 23 | 86 | 55 |
| | 45 | — | 87 | 47 |
| | 58 | — | — | 46 |
| | 60 | 32 | 91 | — |
| | 77 | — | — | 45 |
| | 87 | — | — | 44 |
| | 107 | 46 | — | — |
| | 117 | — | — | 43 |
| | 160 | 55 | — | — |

Examples 5-7

Example 5 was a mixture of 0.46 g A15 and 3 ml of a HAc solution (1.6 M concentration in MeAc) was added to a vial resulting in a catalyst loading of 2.2 g HAc/g A15. Example 6 was a mixture of 0.14 g A15 and 3 ml of a HAc solution (1.6 M concentration in MeAc) was added to a vial resulting in a catalyst loading of 0.68 g HAc/g A15. Example 7 was a mixture of 0.07 g A15 and 3 ml of a HAc solution (1.6 M concentration in MeAc) was added to a vial resulting in a catalyst loading of 0.34 g HAc/g A15. In Examples 5-7, vials were then slurried and stirred, and each was periodically sampled. The vials were septum sealed in order to prevent volatilization of acetaldehyde and stirred in order to optimize contact between solution and A15.

Figure 3:
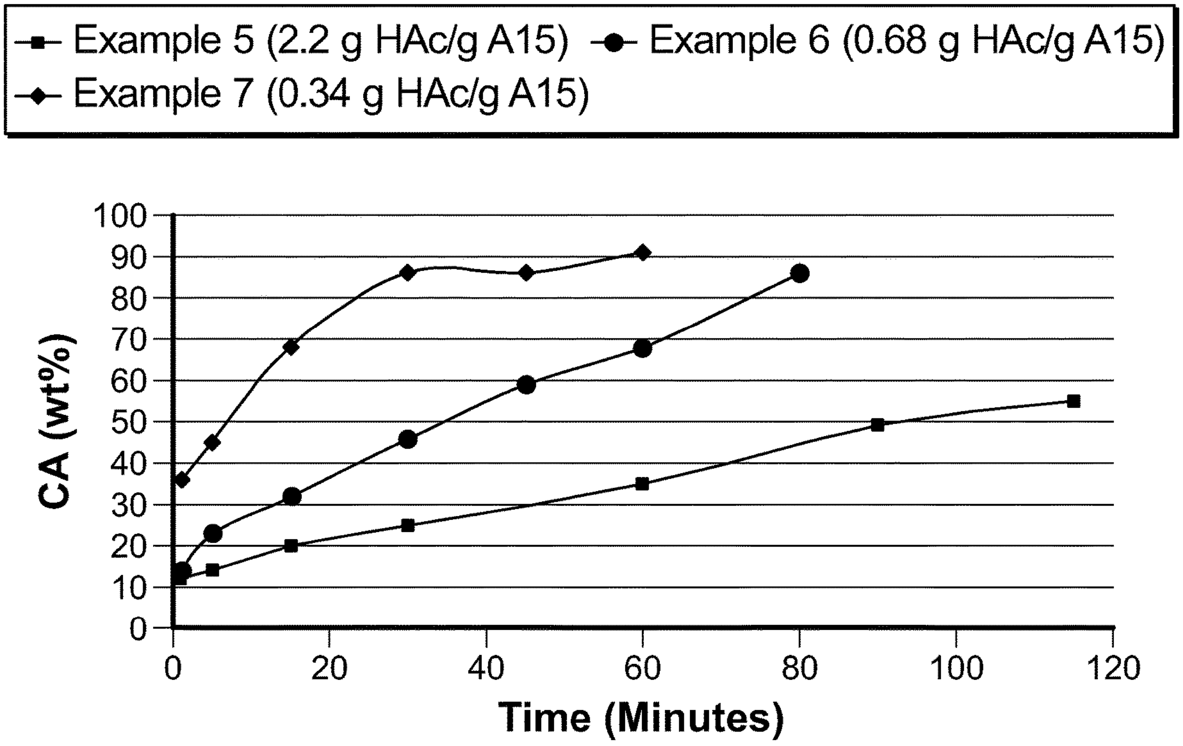
FIG. 3 is an overlaid graph of % crotonaldehyde vs. time for different catalyst loadings in accordance with embodiments of the present techniques.

TABLE 4 and FIG. 3 show how the rate of CA formation can be controlled by varying catalyst loading. Example 5 shows that at a catalyst loading of 2.2 g HAc/g A15, there is a steady increase in the amount of CA to a peak value of 57 wt % at 115 minutes. Example 6 shows that at a catalyst loading of 0.68 g HAc/g A15, the rate of increase is significantly greater than Example 5 reaching a peak value of 85 wt % at 80 minutes. Example 7 shows that at a catalyst loading of 0.34 g HAc/g A15, the rate of increase is much greater than Example 6 reaching a peak value of 92 wt % at 60 minutes. These samples show that CA formation rate is responsive to increases in catalyst loading relative to HAc.

TABLE 4

| | | Weight Percent CA | | |
|---|---|---|---|---|
| Example | | 5 | 6 | 7 |
| A15 Loading (g HAc/g A15) | | 2.2 | 0.68 | 0.34 |
| Time (min.) | 1 | 12 | 14 | 36 |
| | 5 | 14 | 23 | 45 |
| | 15 | 20 | 32 | 68 |
| | 30 | 25 | 46 | 86 |
| | 45 | — | 59 | 86 |
| | 60 | 35 | 68 | 91 |
| | 80 | — | 86 | — |
| | 90 | 49 | — | — |
| | 115 | 55 | — | — |

Examples 8-12

In Example 8, 0.63 g of Amberlite CG-50, a weakly acidic resin with carboxylic acid functionality, was slurried with 3 mLs of 1.6M HAc. This corresponds to 0.33 g HAc/g resin. After 90 minutes of being stirred at 22° C., FTIR analysis showed that all of the HAc remained unreacted.

In Example 9, 1.54 g of zeolite Y was added to 6 mLs of 1.25M HAc. This corresponds to 0.21 g HAc/g zeolite. After 30 minutes stirring at 22° C., FTIR analysis showed that only 32% of HAc had converted to paraldehyde and no crotonaldehyde was present.

Examples 2-7 show that strong acid resins, such as Amberlyst 15, are effective to form both CA and PLD. Example 8 shows that weak acid resins, such as Amberlite, are ineffective to form either CA or PLD. Example 9 shows that acidic zeolites, such as Zeolite Y, are effective to form PLD but not CA.

Flow-Through Bed Experiment

Example 10

One flow through bed experiment was performed. A solution of 0.8 M HAc in methyl acetate was passed through a bed having a bed volume ("BV") of 9.4 ml and a length-to-diameter ratio of 10:1. The bed contained Amberlyst 15. The data for various flow rates are reported in TABLE 5.

TABLE 5 shows nearly complete conversion to CA and no formation of PLD at all flow rates.

TABLE 5

| BV (no.) | Wt % PLD in Eluate | Wt % CA in Eluate |
|---|---|---|
| 1.4 | 0 | 100 |
| 2.1 | 0 | 95 |
| 2.9 | 0 | 90 |
| 3.6 | 0 | 86 |
| 4.4 | 0 | 86 |

The particular embodiments disclosed above are illustrative only, as the process and system may be modified and practiced in different but equivalent manners apparent to those skilled in the art having the benefit of the teachings herein. In the event of conflict between one or more of the incorporated patents or publications and the present disclosure, the present specification, including definitions, controls. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method for removing acetaldehyde from an acetic acid system, comprising:

providing from the acetic acid system a light-ends stream, comprising carbon monoxide, carbon dioxide, acetaldehyde, methyl iodide, methyl acetate, methanol, water, acetic acid, or mixtures thereof;

condensing the light-ends stream in a flask vessel to form one or more liquid phase compositions and a vapor phase composition, wherein the one or more liquid phase compositions comprise a majority, based on a total weight of the light-ends stream, of the water and acetic acid, and the vapor phase composition comprises a majority, based on the total weight of the light-ends stream, of the carbon monoxide and carbon dioxide and a minor portion, based on the total weight of the light-ends stream, of the acetaldehyde, methyl iodide, water, and acetic acid;

contacting the vapor phase composition with a solvent in an absorber to produce an absorber overhead vapor stream and an absorber bottoms liquid stream, wherein the absorber overhead vapor stream comprises carbon monoxide, carbon dioxide, and a first portion of the solvent, and the absorber bottoms liquid stream comprises methyl iodide, acetaldehyde, and a second portion of the solvent; and contacting a reactive feed stream in an acetaldehyde reactor, comprising the absorber bottoms liquid stream, and optionally a polyol compound, with an acid catalyst in to form a reacted stream comprising an aldehyde derivative, wherein the aldehyde derivative is formed by conversion of at least a portion of the acetaldehyde and has a higher boiling point than acetaldehyde.

2. The method of claim 1, wherein the aldehyde derivative is crotonaldehyde, acetal, or a combination thereof.

3. The method of claim 1, wherein the polyol compound comprises a $C_2$-$C_{10}$ diol or triol.

4. The method of claim 1, further comprising removing the aldehyde derivative from the reacted stream.

5. The method of claim 4, wherein the removing comprises:

distilling the reacted stream in an acetaldehyde reactor effluent distillation column to form a distillation overhead stream, comprising methyl iodide, and a distillation bottoms stream, comprising the aldehyde derivative; and discharging the distillation bottoms stream from the acetic acid system.

6. The method of claim 5, further comprising recycling the distillation overhead stream within the acetic acid system.

7. The method of claim 6, wherein the acetic acid system comprises an acetic acid production reactor, and the distillation overhead stream is recycled to the acetic acid production reactor, the acetaldehyde reactor effluent distillation column, or a combination thereof.

8. The method of claim 1, wherein the vapor phase composition comprises less than 1 wt % acetic acid.

9. The method of claim 1, wherein the acid catalyst is an acidic ion exchange resin.

10. The method of claim 1, wherein the acetic acid system comprises a light-ends column, the method further comprising:

feeding a light-ends overhead stream from the light-ends column to a decanter; and withdrawing from the decanter:

one or more liquid phase compositions; and the vapor phase composition.

11. The method of claim 1, further comprising:

condensing a portion of the water and acetic acid in the vapor phase composition to form a condensed portion of the vapor phase composition; and removing the condensed portion from the vapor phase composition.

12. The method of claim 1, wherein the acetic acid system comprises an acetaldehyde reactor having a fixed bed comprising the acid catalyst, and the reactive feed stream is fed to the acetaldehyde reactor.

* * * * *